(12) United States Patent
Downing, Jr.

(10) Patent No.: US 6,601,464 B1
(45) Date of Patent: Aug. 5, 2003

(54) PARTICLE MOMENTUM SENSOR

(76) Inventor: John P. Downing, Jr., 260 Kala Heights Dr., Port Townsend, WA (US) 98368

( * ) Notice: Subject to any disclaimer, the term of this patent is extended or adjusted under 35 U.S.C. 154(b) by 223 days.

(21) Appl. No.: 09/692,832

(22) Filed: Oct. 20, 2000

(51) Int. Cl.$^7$ .............................................. G01N 15/07
(52) U.S. Cl. .................................................. 73/865.5
(58) Field of Search .......................... 73/28.01, 28.05, 73/865.5, 862.68, DIG. 4, 170.25, 170.17; 310/338, 328, 319

(56) References Cited

U.S. PATENT DOCUMENTS

| | | | |
|---|---|---|---|
| 3,167,668 A | | 1/1965 | Nesh |
| 3,700,938 A | | 10/1972 | Bryant |
| 3,805,591 A | * | 4/1974 | Willis et al. |
| 3,816,773 A | * | 6/1974 | Baldwin et al. |
| 4,114,063 A | | 9/1978 | Nelkin et al. |
| 4,114,557 A | * | 9/1978 | De Brey .................... 73/28.01 |
| 4,131,815 A | | 12/1978 | Boatwright |
| 4,240,287 A | | 12/1980 | Mast et al. |
| 4,315,428 A | | 2/1982 | Stuivenwold et al. |
| 4,628,223 A | | 12/1986 | Takeuchi et al. |
| 4,674,337 A | | 6/1987 | Jonas |
| 4,804,007 A | | 2/1989 | Bran |
| 4,904,894 A | * | 2/1990 | Henry et al. ............. 73/DIG. 4 |
| 5,207,090 A | | 5/1993 | Downing, Jr. |
| 5,257,530 A | | 11/1993 | Beattie et al. |
| 5,419,176 A | * | 5/1995 | Walker |
| 5,681,986 A | | 10/1997 | Merk et al. |

OTHER PUBLICATIONS

Markus, Stefan, 1988, "The Mechanics of Vibration of Cylindrical Shells," *Studies in Applied Mechanics* 17, Elsvier, New York, N. Y., pp. 16, 18.

Roa, 1999, "Dynamics of Plates," Marcel Dekker, Inc. New York, N. Y., pp. 74–75.

Young, W.C., 1989, *Roarks Formulas for Stress and Strain Sixth Edition,* Mcgraw Hill, Inc., pp 650–651.

Petrucci, R. and K. Simmons, 1994, "An Introduction to Piezoelectric Ceramics", *Sensors,* May, pp 26–31.

AIRMAR Technology Corporation, 1999, "Piezoflex Polymer Transducers, Specifications," Document # 17–244–01 rev. 02/.

D. Fiore, R. Gentilman, H. Pham, W. Serwatka, P. McGuire and Bowen, L., 1996, "Recent Developments in 1–3 Piezocomposite Transducer Fabrication," Proceedings of the Tenth IEEE International Symposium on Applications of Ferroelectrics, vol. 1, pp 531–534.

Harris, C.M. and C.E. Crede, 1976, *Shock and Vibration Handbook, 2nd Edition,* McGraw–Hill Book Co., Inc., New York, N. Y., pp 2–4 through 2–7 and 2–14 through 2–17.

Wiberg, P.L. and J.D. Smith, 1987, "Calculations of the Critical Shear Stress for Motion of Uniform and Heterogeneous Sediments," Water Resources Research, vol. 23(8), pp 1471–1480.

Bridge, J.S. and Dominic, D.F., 1984, "Bed Load Grain Velocities and Sediment Transport Rates," *Water Resources Research,* vol. 20(4), pp 476–490.

* cited by examiner

*Primary Examiner*—Robert Raevis
(74) *Attorney, Agent, or Firm*—Donald W. Marks

(57) ABSTRACT

A particle momentum detector has a massive support with a flat surface on which is mounted a piezoelectric member supporting a flat low mass plate resistant to deformation by impinging particles. The low mass plate has a rigidity suppressing multiple mode vibration of the plate. The piezoelectric member generates a damped oscillating electrical signal when a particle impinges upon the plate. A circuit integrates a portion, such as the first half cycle, of the damped oscillating electrical signal to determine momentum of the particle.

19 Claims, 7 Drawing Sheets

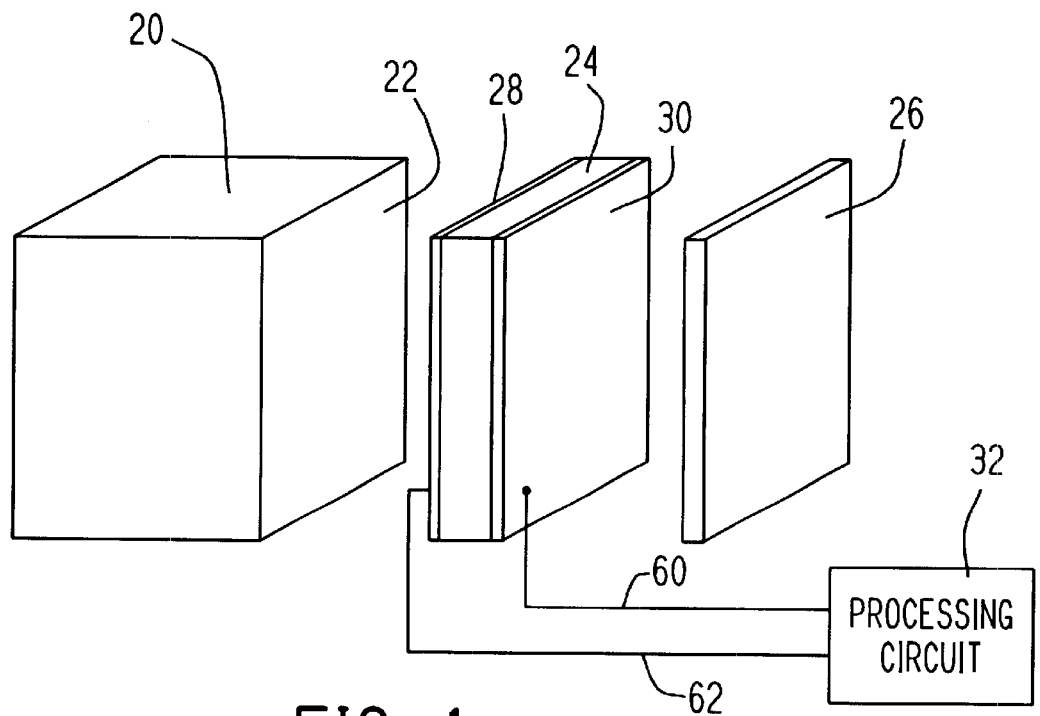
FIG. 1
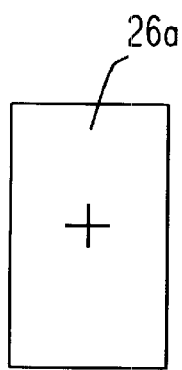 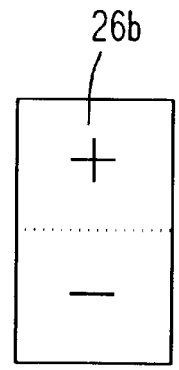 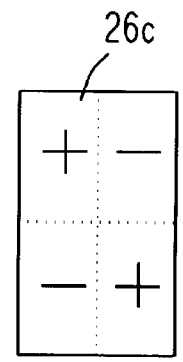
FIG. 2A  FIG. 2B  FIG. 2C

PARTICLE MOMENTUM SENSOR

BACKGROUND OF THE INVENTION

The present invention relates of a device for measuring the momentum of a dense particle, such as a stone, gravel particle, ball bearing, or the like, being carried by a moving fluid such as air, water, fuel, lubricant, etc., and particularly to a device for measuring momentum of gravel particles moving in a stream, surf or down a steep hillside.

The prior art includes particle sensors for sensing the number of particles being carried by a stream. This type of sensor is a hollow cylinder or pipe designed to have one end embedded in a stream bed with its other end extending into the moving water. Impacts or pings produced by gravel particles impinging on the upper end of the sensor are counted. Mass and volume transport of gravel in the stream can be calculated from the ping count when average particle size and weight are known. However average particle size and weight are often not known or often change when stream conditions change.

A sensor for determining the energy (momentum) of sand or fracture particles in oil and gas production flow streams is known in the prior art. This sensor determines the area within the acoustic vibration envelope produced by impingement of a particle on cylindrical probe extending into the pipe carrying the flow stream to determine the particle energy.

SUMMARY OF INVENTION

An object of the invention is to construct an improved particle momentum sensor for measuring the momentum of dense particles, such as a stone, gravel particle, ball bearing, or the like, being carried by a moving fluid such as air, water, fuel, lubricant.

Another object of the invention is to enable detection of the momentum of closely spaced particles in a moving fluid.

These and other objects are achieved in a particle momentum sensor having a massive support with a flat surface on which is mounted a piezoelectric member supporting a flat low mass plate resistant to deformation by impinging particles and having a rigidity suppressing multiple mode vibration of the plate. The piezoelectric member generates a damped oscillating electrical signal when a particle impinges upon the plate. A circuit integrates a portion of the damped oscillating electrical signal to determine momentum of the particle.

Additional features of the invention include the integration of the first half cycle of the damped oscillating electrical signal to determine particle momentum; a system Q of about 2 to enable detection of closed spaced particles; a fundamental oscillating frequency of the plate and its mounting being sufficiently high such as 10 kHz to 20 kHz for enabling detection of closely timed impingements of particles; the use of two flat plates or joined plate portions disposed at an angle such as 90° relative to each other; and the mounting of the piezoelectric member with the flat plate in a recess in one side of a metal bar having a rectangular cross section.

Other advantages and features of the present invention will be apparent from the following detailed description and the accompanying drawings.

BRIEF DESCRIPTION OF DRAWINGS

FIG. 1 is an exploded schematic illustration of a particle momentum sensor constructed in accordance with the present invention.

FIG. 2A is an illustration of a single mode vibration of a plate.

FIG. 2B is an illustration of a multi-mode vibration of a plate.

FIG. 2C is an illustration of another multi-mode vibration of a plate.

DETAILED DESCRIPTION

Figure 3:
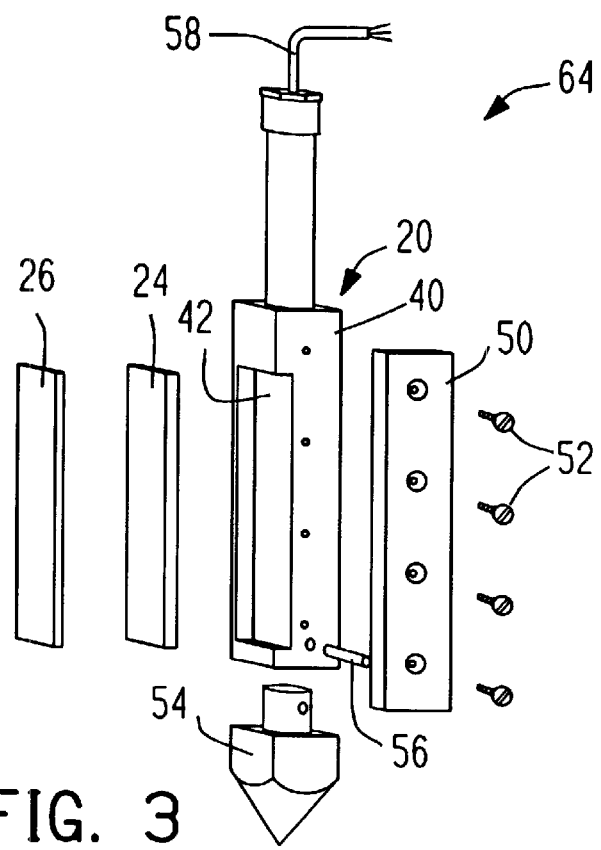
FIG. 3 is an exploded perspective view of one embodiment of the detector portion of a particle momentum sensor of the present invention.

As shown in FIG. 1, a particle momentum sensor in accordance with the invention includes a massive support 20 having a flat surface 22 on which a piezoelectric member 24 is mounted with a flat low mass plate 26 being supported in engagement with the piezoelectric member 24. The flat low mass plate 26 is resistant to deformation by impinging particles and has a rigidity suppressing multiple mode vibration or flexing of the plate. The piezoelectric member 24 has electrodes 28 and 30 on its opposite faces electrically connected to a processing circuit 32. A damped oscillating electrical signal is generated by the piezoelectric member 24 when a particle impinges upon the plate 26. A portion of this damped oscillating electrical signal is integrated by the processing circuit 32 to determine momentum of the particle. The flat plate 26, being resistant to deformation and having rigidity suppressing multimode oscillation or flexing of the plate, is found to produce signals which reflect particle momentum substantially more accurately than round or cylindrical probes; particles engaging central and side portions of a cylindrical probe impart different forces to the probe due to different angles of engagement whereas particles engage the present flat plate 26 at the same angle whether the engagement is at the center or edge of the plate.

The support member 20 is massive and rigid so that the device remains stationary and the impact force from a particle on the plate 26 is efficiently converted to electrical signals by the piezoelectric member 24. This support member 20 can be a metal member having thickness or dimensions providing a mass which is generally ten (10) times the mass of the plate 26 and preferably twenty (20) times the mass of the plate 26. If to be exposed to moisture, the support member 20 is made of a corrosion resistant material or coated with a corrosion resistant material.

The flat plate 26 is made of a hard, abrasion-resistant material which will not be permanently deformed by impacting particles as well as being corrosion resistant. Many metals, such as 17-4 stainless steel, stellite alloy, etc., are suitable. The mass of the plate 26 is low so that the force of impacting particles is readily transferred to the piezoelectric member 24. The plate 26 has rigidity to suppress multimode vibration. In FIG. 2A the plate 26a has a single mode of vibration or flexing, i.e., an impacting particle moves the entire plate with little flexure. In FIG. 2B the plate 26b has a multimode of vibration or flexing, i.e., a particle impacting the upper portion of the plate 26b initiates an oscillatory motion of the upper portion of the plate while due to the flexibility of the plate the lower portion of the plate has an oscillatory motion which is 180° out of phase with the upper portion. Thus forces transferred to the upper and lower portions of piezoelectric member by the plate 26b produce signals which cancel each other. Another multimode vibration is illustrated in FIG. 2C. The rigidity or stiffness of the flat plate 26 suppresses the multimode vibrations illustrated in FIGS. 2b and 2c as well as other higher order multi-modes of vibration. The plate 26 can be oriented at an angle from 30° to 90° relative to the direction of stream flow. At 30° the force of each impact will be about 50% of the force at 90° and at 60° the force of each impact will be about 87% of the force at 90°. An angle less than 90° is preferred to ensure that the particles bounce away from the flat plate 26 after impact.

The piezoelectric member 24 can be a piezoelectric ceramic plate, a piezoelectric polymer such as PVDF piezoelectric polymer or a piezoelectric ceramic/polymer composite such as 1–3 ceramic/polymer composite. The piezoelectric ceramic materials generally have the highest sensitivity but also have the highest Q (the number of cycles for an oscillation to decay in amplitude by a factor 0.37). Composites have high sensitivity and about 60% lower Q than conventional PZT materials. PVDF has the lowest sensitivity and the lowest Q and is easier to form and the least expensive.

It is desirable that the detector system have a low Q as well as a relatively high fundamental frequency of natural oscillation in order that vibration of the detector from a particle impact will decay rapidly. The vibration of an impact must decay below the threshold value before another impact can be detected. Generally this system Q should be less than about 4 and preferably less than about 2. In one preferred example, the system Q is about 2. It is noted that the Q of the piezoelectric member 24 is not the sole factor in determining the Q of the system. The plate 26 and the mounting of the plate 26, such as by a flexible sealant, reduce the Q of the system. A fundamental oscillation frequency for the plate 26 in the range from 10 kHz to 20 kHz, such as 17 kHz, is suitable.

In a first embodiment, the piezoelectric member 24 is bonded by an adhesive (not shown) on one face to the flat face 22 of the support 20 and the flat plate 26 is bonded by an adhesive (not shown) on the opposite face of the piezoelectric member 24. Suitable adhesives include epoxy resins with a suitable metal primer. Additionally the edges of the piezoelectric member 24 and its electrodes 28 and 30 as well as the edges of the seams between the members 20, 24 and 26 are sealed with a flexible sealant such as a soft, compliant polyurethane compound (not shown) to prevent moisture or other fluid contact. The piezoelectric member 24 and the flat plate 26 are illustrated as being rectangle with the member 24 and the plate 26 being generally the same size and shape. However the member 24 and plate 26 can have many different shapes and need not be the same dimensions. Having rectangular dimensions enables relatively easy construction and easy calculation of the cross sectional area being monitored.

Figure 4:
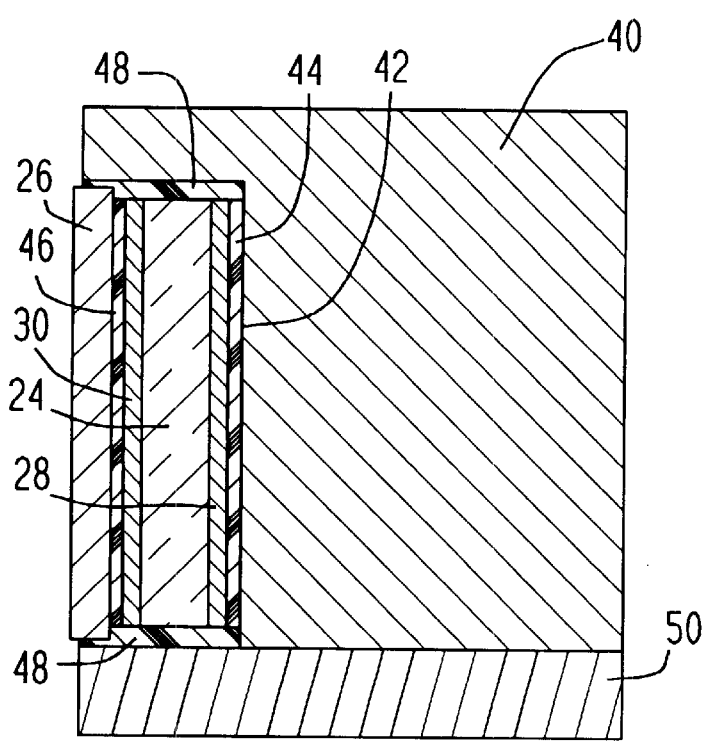
FIG. 4 is a cross sectional illustration of the detector portion of the embodiment of FIG. 3.

A second embodiment is illustrated in FIGS. 3 and 4 wherein the massive support is formed by a bar 40 with a rectangular cross section having a recess 42 in which the piezoelectric member 24 is mounted by an adhesive layer 44 to the flat bottom surface of the recess 42 and the flat plate 26 is mounted by an adhesive layer 46 to the piezoelectric member 24. The edges of the piezoelectric member 24 and flat plate are sealed by a soft compliant sealant 48. One side edge of the recess 42 opens in the side of the bar 40 and is closed by a plate 50 attached by screws 52 for enabling easy assembly of the detector portion of the particle momentum sensor. A pointed member 54 is attached to the lower end of the sensor such as by a pin 56 to enable the bottom end of the sensor to be inserted into a stream bed. A cable 58 with the wires 60 and 62 (FIG. 1) connected to the electrodes 28 and 30 of the piezoelectric member 24 passes from an upper pipe portion of the detector portion 64 of the particle momentum sensor for connection to the processing circuit 32 which is external in this embodiment.

Figure 5:
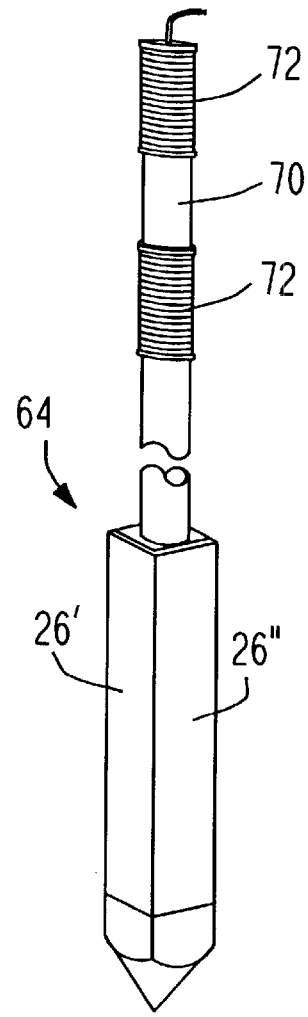
FIG. 5 is a perspective view, with a portion broken away, of a second embodiment of the particle momentum sensor of the present invention.

A third embodiment shown in FIG. 5 has a handle 70 with a pair of hand grips 72 for enabling the detector portion 64 of the particle momentum sensor to be held in a stream to measure moving particles. Additionally this third embodiment has two flat plates 26' and 26" which extend at a reflex angle, i.e., the angle between the exposed sides being greater than 180° and less than 360°, preferably between 240° and 300° such as 270° relative to each other. The plates 26' and 26" can either be joined at their vertex as shown or be separate. The two plates 26' and 26" are mounted similar to the plate 26 of the first and second embodiments with epoxy resin to flat piezoelectric members which in turn are mounted by epoxy resin to flat surfaces of the massive support. The detector portion 64 is oriented with the vertex of plates 26' and 26" pointed toward the direction from which the fluid stream water is flowing.

Figure 6:
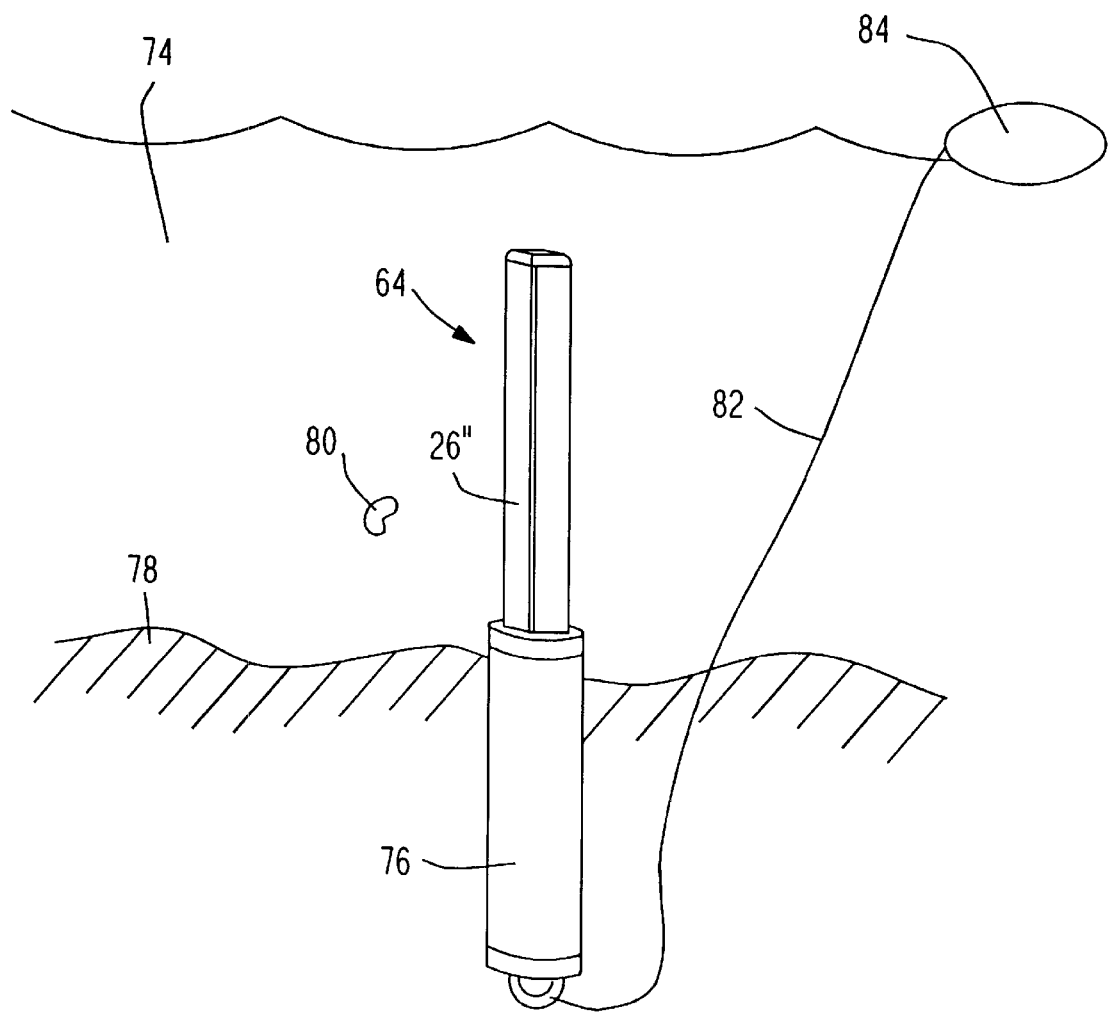
FIG. 6 is a perspective view of a third embodiment of the particle momentum sensor of the present invention within a stream.

In FIG. 6, a fourth embodiment has the detector portion 64 extending upward into stream 74 from a sealed lower casing 76 which is buried in a stream bed 78. The lower sealed casing 76 contains the processing circuit 32 as well as batteries (not shown) and recording facilities (not shown) for recording the momentums of particles 80 impinging on the flat plates (only plate 26" shown) of the detector 64. The particle momentum sensor of FIG. 6 includes a tether line 82 attached to a buoy 84 for marking the position of the particle momentum sensor.

Figure 7:
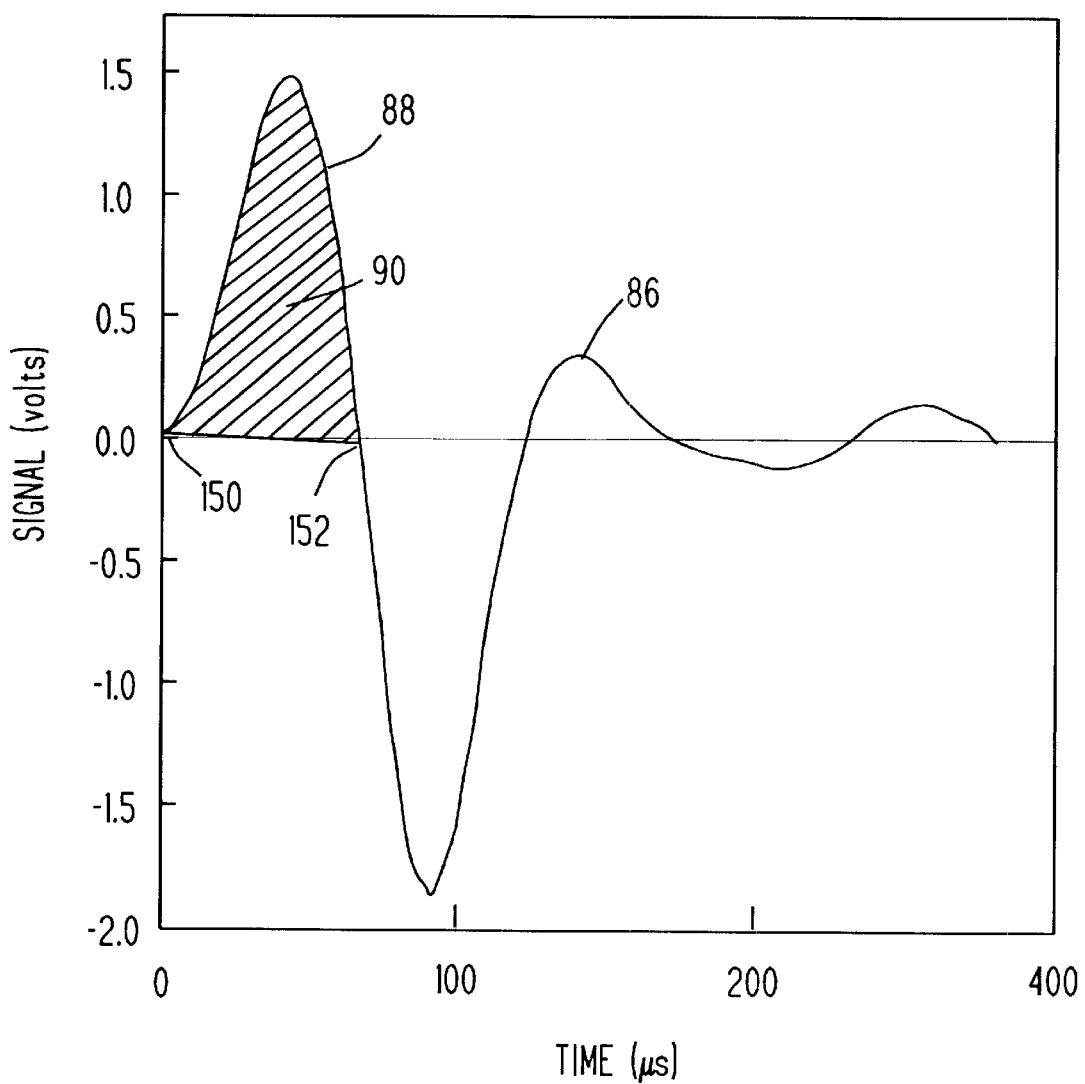
FIG. 7 is a waveform diagram of an electrical signal produced by a piezoelectric member in the particle momentum sensor of the present invention.

FIG. 7 shows an example waveform 86 of an electrical signal produced by the piezoelectric member 24 and applied to the processing circuit 32. The processing circuit 24 integrates a portion of this signal, such as the first half cycle 88 corresponding to the area 90. It is found that this integration of a selected portion of the waveform is an accurate measure of the momentum of a particle impinging on the flat plate 26. While integration of the first half cycle is preferred, the second half cycle could just as easily be integrated or a full wave rectification of the whole first cycle could be integrated to produce an accurate measure of the momentum of the particle impinging on the flat plate. It is noted that the signal 86 drops rapidly due to a low system Q, i.e., a Q equal to or less than about 2, so that another particle impingement can by measured after only a very short period of time.

Figure 8:
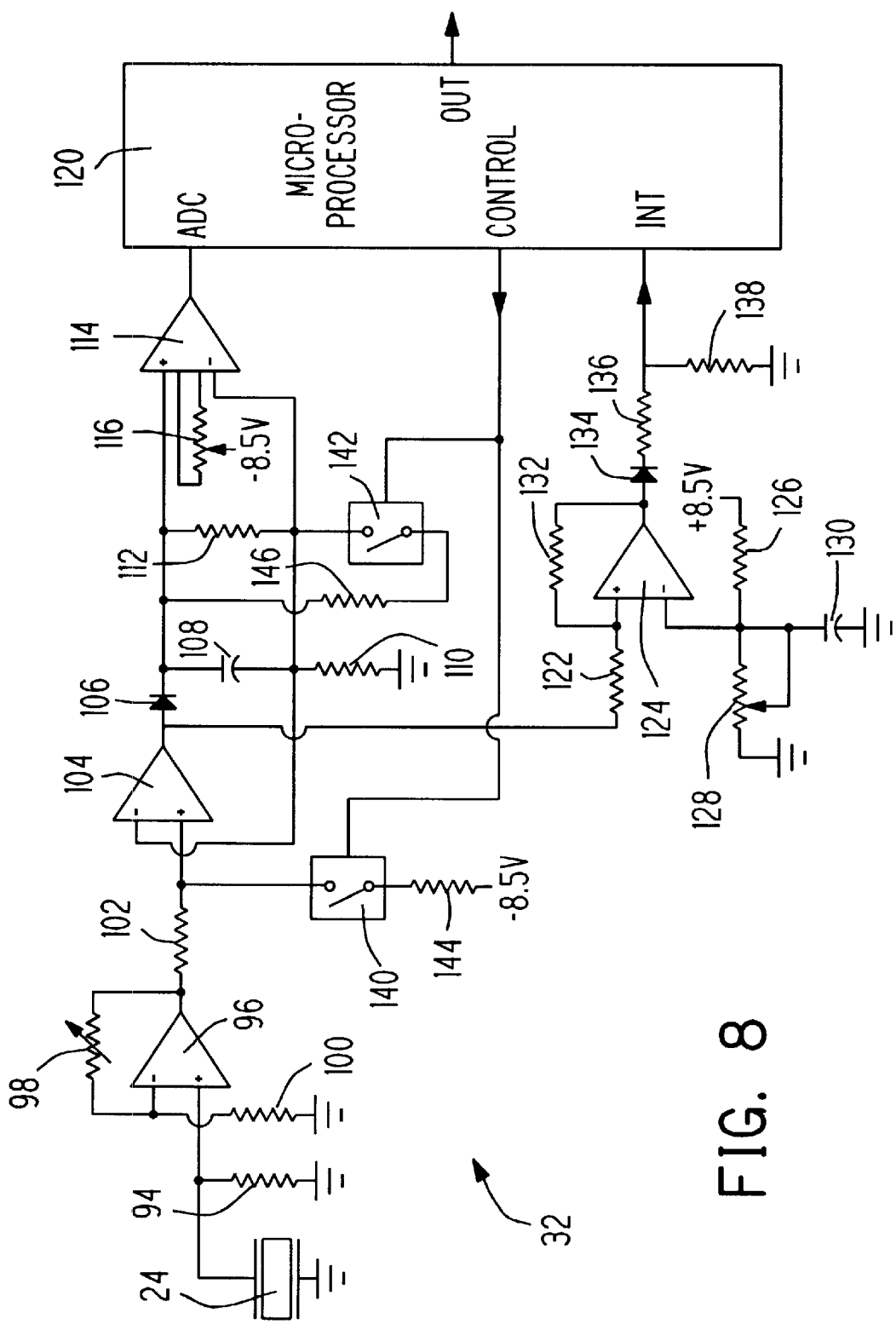
FIG. 8 is a schematic drawing of an electrical circuit employed in the particle momentum sensor of the present invention.

An example of the processing circuit 32 is shown in FIG. 8 wherein the output of the piezoelectric 24 across a resistor 94 is applied to an input of an amplifier 96 controlled by a feedback resistor 98 and a resistor 100 to ground. The output of the amplifier 96 is connected by a resistance 102 to an input of an integrating circuit including operational amplifier 104, a diode 106 connected between the output of the amplifier 104 and one side of a capacitor 108 which has its other side connected to the negative input of the amplifier 104 and a resistance 110 to ground. A stabilizing resistance 112 is connected across the input of an amplifier 114 connected across the capacitor 108 and includes an output offset adjusting potentiometer 116. The output of the amplifier 114 is connected to an input of an analog to digital convertor portion of a microprocessor 120. The output of the amplifier 104 is also connected by a resistance 122 to an positive input of an amplifier 124 which has its negative input connected to a threshold setting circuit including a resistance 126 and a potentiometer 128 connected between a positive voltage source and ground and with the slider of the potentiometer connected to the negative input and one side of a capacitor 130 to ground. A feedback resistance 132 is connected between the output and the positive input of the amplifier 124 so that the amplifier operates as a trigger circuit, i.e., goes positive when the input exceeds the threshold voltage and goes negative when the input drops below zero by the threshold voltage. The output of the amplifier 124 is applied by a diode 134 to series resistances 136 and 138 to ground with the junction between resistances 136 and 138 connected to an interrupt input of the microprocessor 120. A control output of the microprocessor is connected to control inputs of electronic switches 140 and 142 which, when operated, connect a negative voltage from resistance 144 to the positive input of amplifier 104 and connect a discharge resistance 146 across the capacitor 108.

In operation of the processing circuit 32, the amplifier 124 is triggered positive when the input signal 86 exceeds the threshold setting, point 150 in FIG. 7, which is adjusted to prevent triggering by noise in the absence of any particle impinging on the detector 64. The microprocessor 120 then begins a timing period. The positive signal or first half cycle of the impact is integrated by the output of the amplifier charging the capacitor 108. Subsequently when the input signal drops below zero volts by a voltage equal to the threshold voltage, the amplifier 124 is triggered negative which is sensed by the microprocessor which then proceeds to perform the analog to digital conversion procedure to read the voltage stored on the capacitor 108. Also the microprocessor 120 determines whether the timing period of the integration exceeds a minimum time; timing periods less than the minimum time are considered as noise and rejected as not being caused by particle impact. Readings of charges across the capacitor 108 are converted to particle momentums and stored in a memory or other recording device. After the reading of a particle momentum voltage has been taken, the control output of the microprocessor operates the switches 140 and 142 force the amplifier 104 negative and to discharge the capacitor 108. After the capacitor is discharged the microprocessor 120 releases the switches to enable the detection and reading of another particle impact on the particle momentum sensor.

Figure 9:
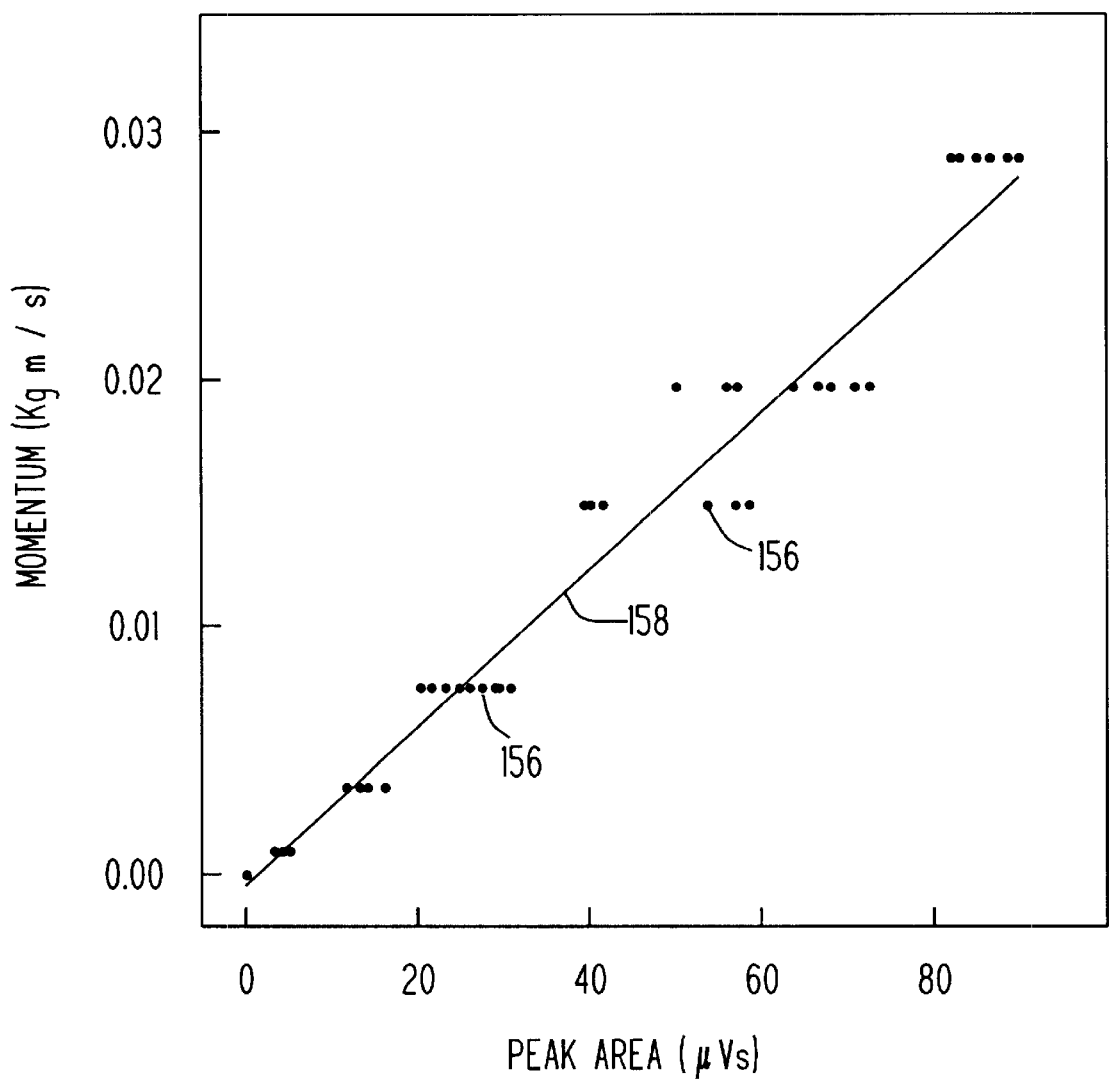
FIG. 9 is a graph illustrating calibration of a particle momentum sensor of the present invention.

FIG. 9 shows a typical calibration of the particle momentum sensor. Particles, such as ball bearings, are directed, such as being dropped from known heights, onto the flat plate 26 of the particle momentum sensor. Readings of the integrated voltages across the capacitor 108 are plotted as dots 156 for various known momentums of the particles. From this plot of dots 156, a curve 158 can be computed and used by the microprocessor 120 to determine the momentums of particles impinging on the flat plate 26 of the particle momentum sensor. It is noted that different calibration curves are used depending upon the angle that the flat plate 26 has relative to the movement of the stream.

In some applications, such as measuring gravel motion on a stream bed, it may be desired to estimate mass or volume flux with the particle momentum sensor and stream information. To do this the size-dependent particle velocity is estimated from flow conditions, sediment size, and stream properties, mainly the local bed slope. The device of FIG. 6 when fixed in a stream bed as shown and equipped with a pressure sensor to measure water depth can make such a measurement. The friction velocity, $u_*$, can be determined continually from the acceleration of gravity, g, stream bed slope, s, and water depth h, as $u_* = \sqrt{gsh}$. The critical friction velocity required to move a particle of a given size class (i), $u_i$, can be determined. The sediment size distribution, D(i) can be determined by direct measurement during low flow conditions. Using the equation $V_i = \alpha(u - \beta u_i)$ where $\alpha$ and $\beta$ are constants and u is stream velocity, particle velocities $V_i$ can also be continually determined. In a practical measurement situation, the proportion of the total particle momentum measured in a period of time, say 5 to 60 minutes depending on transport conditions, is taken as the proportion of particles in that size class. This is a number between 0 and 1.0. Each momentum class is then divided by the velocity of that size particle to get the mass in motion during the measurement period. The total over all size classes give the mass flux for the period. The volume flux can be easily obtained by dividing the mass by the average particle density. If the size distribution, bed slope, and device cross section are known prior to deployment, the microprocessor can do these calculations in real time and store the computed flux with the other data. The constants $\alpha$ and $\beta$ vary over a limited range so some calibration tests may be required to determine the best values for a particular stream.

Figure 10:
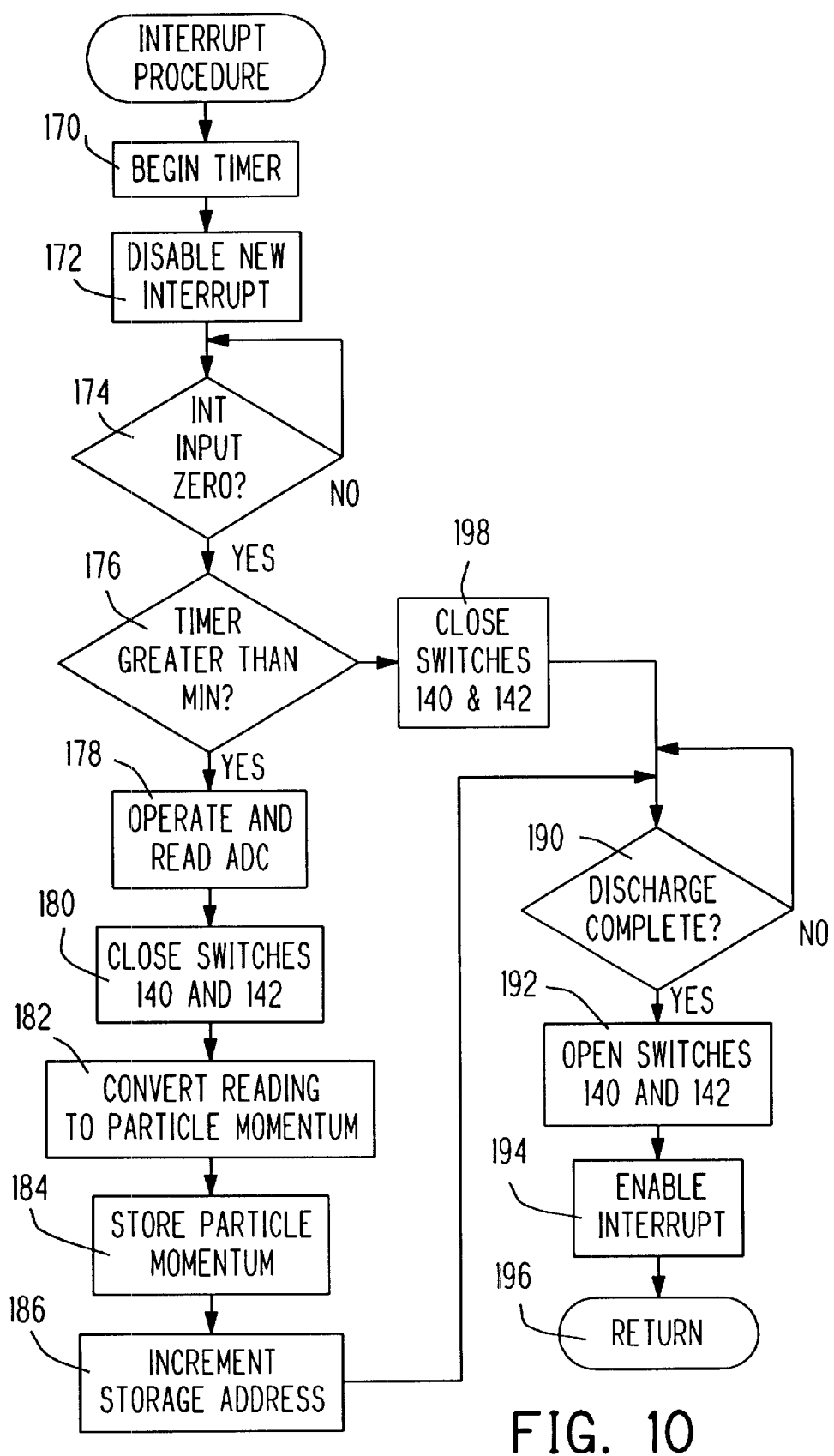
FIG. 10 is a flow diagram of an interrupt procedure in a microprocessor of the circuit of FIG. 8.

An interrupt procedure in the microprocessor 120 called by the positive going signal from the threshold detector 124 is shown in FIG. 10. In step 170, a timer is started to measure the duration of the first half cycle of the incoming signal from the piezoelectric. Further interrupts are disabled in step 172 during the measuring of the incoming signal. Determination of the threshold input becoming zero is made in step 174 and, if false, continued until true. The duration of the first half cycle of the incoming signal as measured by the timer started in step 170 is compared with a minimum duration MIN in step 176. This minimum value MIN is determined to be the minimum duration that a particle will engage the flat plate 26 and values less than MIN are rejected as noise signals. When step 176 is true, the analog to digital converter in the microprocessor is operated and the voltage across the capacitor 108 is read in step 178. In step 180 the switches 140 and 142 are closed to discharge the capacitor 108. The reading from the analog to digital convertor is converted to a particle momentum value in step 182 such as by an equation or a table based on the curve 158. This calculated particle momentum value is store in memory in step 184 at the memory address pointed to by step 186 in a previous reading or by an initialization procedure upon startup. Step 190 is repeated until it is determined that discharge of the capacitor 108 is complete such as by a minimum time lapse or reading of zero from the analog to digital converter. When the capacitor 108 is completely discharged, the switches 140 and 142 are opened in step 192, interrupts are enabled in step 194 and the procedure returns from the interrup procedure in step 196. If step 176 is false indicating that the incoming signal is noise, the procedure branches to step 196 where the switches 140 and 142 are closed and then proceeds to the step 190.

Alternatively, the measurement of particle mass in transport can be made in the following way.

1. The momentums of individual particles could be stored in memory during the observation period.
2. The microprocessor can compute $u_*$, and from the known size distribution, $u_s(i)$ the velocities of particles in size classes i.
3. Then, the microprocessor can sort the particle momentums into i bins to give the momentum measured in a size class during the observation period.
4. The total momentum in a size class divided by the size-class velocity gives the mass in motion of the class.

Since many modifications, variations and changes in detail can be made in the embodiments described above and shown in the accompanying drawings, it is intended that the above description and accompanying drawings be interpreted as only illustrative of the invention.

What is claimed is:

1. A particle momentum sensor comprising:

a massive support having a flat surface;

a flat plate resistant to deformation by impinging particles and having a rigidity suppressing multiple mode vibration of the plate said massive support having a mass substantially greater than the mass of said flat plate;

a piezoelectric member mounted between the plate and the flat surface of the support for generating a damped oscillating electrical signal when a particle impinges upon the plate; and means for integrating a portion of the damped oscillating electrical signal to determine momentum of the particle.

2. A particle momentum sensor as claimed in claim 1 wherein the plate is rectangular.

3. A particle momentum sensor as claimed in claim 2 wherein the integrating means integrates an area within one-half cycle of the damped oscillating electrical signal.

4. A particle momentum sensor as claimed in claim 3 wherein the one-half cycle being integrated is a first half cycle exceeding a threshold.

5. A particle momentum sensor as claimed in claim 4 wherein the particle sensor has a system Q preferably less than about 2 wherein Q is the number of cycles for an oscillation to decay in amplitude by a factor 0.37.

6. A particle momentum sensor as claimed in claim 3 wherein the particle sensor has a system Q preferably less than about 2 wherein Q is the number of cycles for an oscillation to decay in amplitude by a factor 0.37.

7. A particle momentum sensor as claimed in claim 1 wherein the integrating means integrates an area within one-half cycle of the damped oscillating electrical signal.

8. A particle momentum sensor as claimed in claim 7 wherein the one-half cycle being integrated is a first half cycle exceeding a threshold.

9. A particle momentum sensor as claimed in claim 1 wherein the particle sensor has a system Q generally less than about 4 wherein Q is the number of cycles for an oscillation to decay in amplitude by a factor 0.37.

10. A particle momentum sensor as claimed in claim 9 wherein the particle sensor has a system Q preferably less than about 2 wherein Q is the number of cycles for an oscillation to decay in amplitude by a factor 0.37.

11. A particle momentum sensor as claimed in claim 1 wherein the particle sensor has a system Q of about 2.

12. A particle momentum sensor as claimed in claim 1 wherein the support includes a metal bar with a rectangular cross section wherein one side of rectangular bar includes a recess receiving the piezoelectric member and the flat plate.

13. A particle momentum sensor as claimed in claim 12 wherein the recess, the piezoelectric member and the flat plate are all rectangular and elongated in shape.

14. A particle momentum sensor as claimed in claim 1 wherein:

the massive support has a pair of flat surfaces extending a reflex angle relative to each other;

there are two flat low mass plates resistant to deformation by impinging particles and having a rigidity suppressing multiple mode vibration of the plates; and there is a piezoelectric member is mounted between each of the plates and a corresponding on of the flat surfaces of the support for generating a damped oscillating electrical signal when a particle impinges upon either of the plates.

15. A particle momentum sensor as claimed in claim 14 wherein the two plates are joined at their vertex.

16. A particle momentum sensor as claimed in claim 15 wherein the reflex angle is 270°.

17. A particle momentum sensor as claimed in claim 14 wherein the reflex angle is 270°.

18. A particle momentum sensor comprising:

a massive support having a flat surface;

a flat low mass plate resistant to deformation by impinging particles and having a rigidity suppressing multiple mode vibration of the plate;

a piezoelectric member mounted between the plate and the flat surface of the support for generating a damped oscillating electrical signal when a particle impinges upon the plate;

the mass of the support being generally greater than 10 times the mass of the plate; and means for integrating a portion of the damped oscillating electrical signal to determine momentum of the particle.

19. A particle momentum sensor as claimed in claim 18 wherein the mass of the support is preferably greater than 20 times the mass of the plate.

* * * * *